United States Patent [19]

Shoesmith

[11] Plant 5,064

[45] Jun. 28, 1983

[54] CHRYSANTHEMUM NAMED TIGER

[75] Inventor: May Shoesmith, Westfield, England

[73] Assignee: Pan-American Plant Company, Parrish, Fla.

[21] Appl. No.: 312,944

[22] Filed: Oct. 19, 1981

[51] Int. Cl.[3] ..... A01H 5/00

[52] U.S. Cl. ..... Plt./78

[58] Field of Search ..... Plt./78, 79

*Primary Examiner*—Robert E. Bagwill

*Attorney, Agent, or Firm*—Chas. W. Rummler

[57] ABSTRACT

A new button type chrysanthemum cultivar distinguished by its profuse production of small, pom pom shaped flowers of a light bronze color, its capability for year around production with an eight-week response, in small 4 to 4½ inch pots, and its adaptability as an excellent garden mum capable of a beautiful display of color in the Fall.

4 Drawing Figures

BACKGROUND OF THE NEW PLANT

This new chrysanthemum was discovered by me at West Chicago, Ill., as a seedling of unknown parentage growing in a field of miscellaneous seedlings planted with the object of finding new varieties of unusual characteristics suitable for the commercial market. This plant was selected because of its profuse production of flowers having a unique light bronze color and asexual propagation of this plant under my direction at West Chicago, Ill., through successive generations, has demonstrated that the novel characteristics of this plant hold true and appear to be firmly fixed. Commercial production of this new plant by means of cuttings is now being carried on at West Chicago, Ill., and at Parrish, Fla.

DESCRIPTION OF THE DRAWINGS

This new chrysanthemum cultivar is illustrated by the accompanying drawings, of which sheet 1 is a full color photographic view showing a field of this plant in full bloom; sheet 2 is a photographic close-up face view of flowers of this plant which has been hand painted to show the true colors of the blooms; sheet 3 is a machine copy of typical leaves of this new variety showing the top side of the leaves; and sheet 4 is a machine copy of the said leaves showing the bottom or back side of the leaves.

DESCRIPTION OF THE NEW PLANT

The following is a detailed description of my new chrysanthemum cultivar based upon observations of plants grown at West Chicago, Ill., and made in the Spring of 1981, the color designations being according to The R.H.S. Colour Chart published by The Royal Horticultural Society of London, England.

THE PLANT

Origin: Seedling.
Parentage: Unknown.
Classification:
- *Botanic.*—*Chrysanthemum morifolium.*
- *Commercial.*—Garden Mum.

Form: Perennial, herbaceous bush of mound to semi-upright shape.
Height: About ¾ to 1 meter.
Growth: Strong and vigorous with a rapid growth rate.

Branching character: Normal.
Foliage:
- *Quantity.*—Abundant.
- *Size of leaf.*—From small to about 70 mm. long and about 55 mm. wide.
- *Shape of leaf.*—Ovate with cleft margins.
- *Texture.*—Leathery.
- *Venation.*—Pinnate.
- *Color.*—Upper side — 147A. Under side — 147B.
- *Leaflets.*—Many of various sizes.

THE BUD

Form: Globular.
Size: Variable in both diameter and length.
Opening rate: Typical chrysanthemum.
Color of florets:
- *When phyllaries first divide.*—13A.
- *When petals begin to unfurl.*—13A.

Phyllaries:
- *Number.*—About 13.
- *Shape.*—Lanceolate.
- *Color.*—147B.

Peduncle: Erect and of various lengths.
- *Aspect.*—Pubescent.
- *Color.*—147B.

THE FLOWER

Blooming habit: Intermittent and profusely in the Fall as a garden plant.
Blooms:
- *Size.*—Small. Diameter — About 20 to 30 mm. Depth — About 10 to 20 mm.
- *Borne.*—Cyme.
- *Shape.*—When bloom first opens — cup-shaped. When bloom matures — Globular. A button pom pom with very few disc florets borne on a capitulum surrounded by an involucre of bracts.

Petalage:
- *Ray florets.*—Many.
- *Disc florets.*—Few.
- *Arrangement.*—Imbricated.
- *Form.*—Obcordate with obtuse apex and entire margins.

Texture: Soft.
Appearance: Satiny.
Color:

*Body base and bottom side.*—13A. Color varies somewhat depending upon the light intensity and temperature.

Persistence: The florets hang on and dry.

Peduncle: Strong and upright and of various lengths.

*Color.*—147B.

Fragrance: Typical chrysanthemum.

Lasting quality: Three to four weeks on the plant.

REPRODUCTIVE ORGANS

Stamens:

*Number.*—Five.

*Arrangement.*—Syngenesious.

*Anthers.*—Size — Insignificant. Color — Yellow.

*Filaments.*—Length — Insignificant. Color — Yellow.

*Pollen.*—Color — Yellow.

Pistils:

*Number.*—One for each floret.

*Styles.*—Length — Various. Color — Yellow.

Stigmas:

*Color.*—Yellow.

Ovaries: Inferior, bicarpellate.

This plant is particularly suitable for year around production in small four to four and a half inch pots and generally has an eight-week response. This plant also makes an excellent garden mum and if planted as vegetative cuttings and pinched until flower initiation, it will make an excellent display of color in the Fall.

I claim:

1. A new and distinct chrysanthemum cultivar, substantially as herein shown and described, characterized by its small button type of inflorescence having a distinct light bronze color, by its profuse blooming habit, and by its capability for year around small pot production.

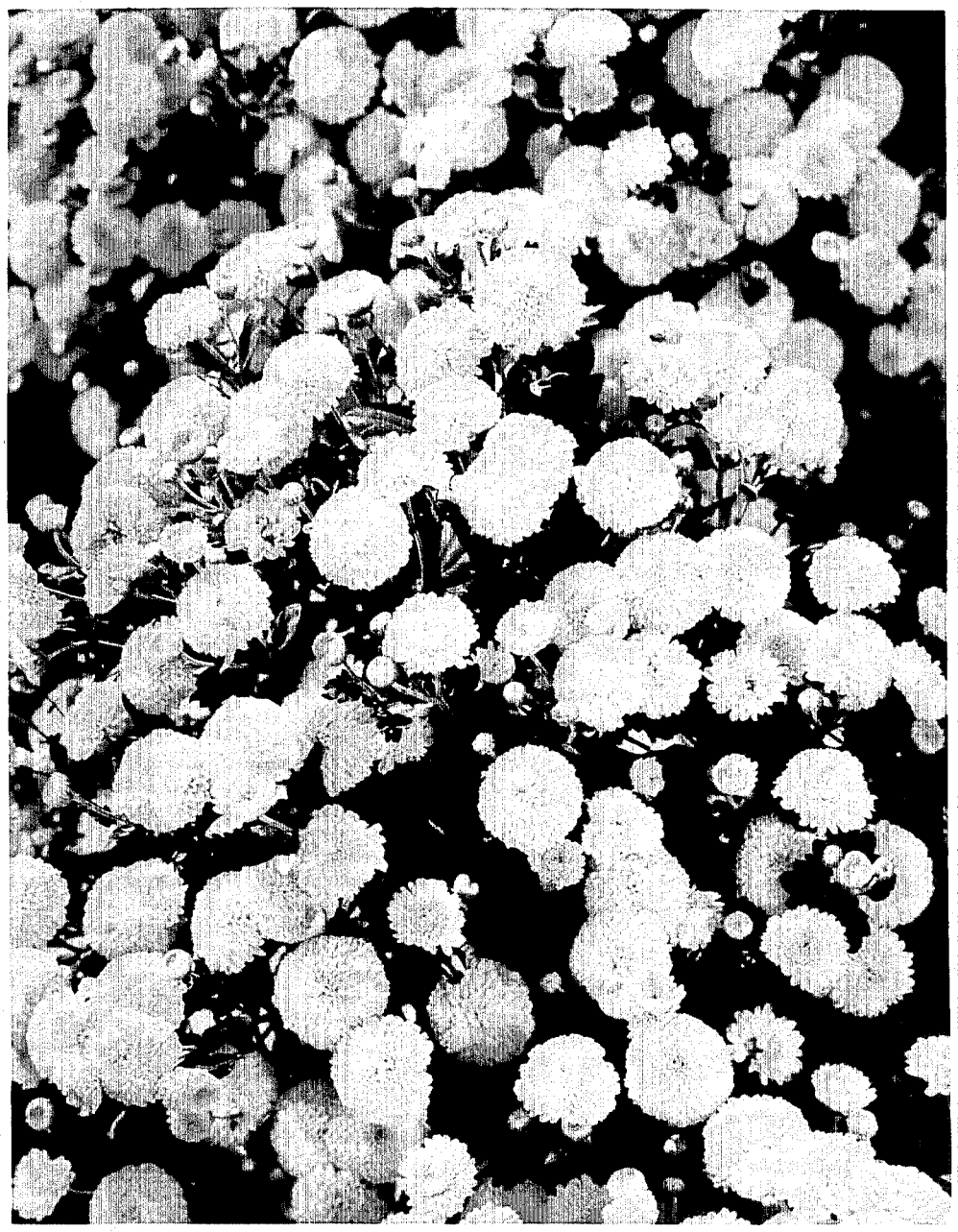

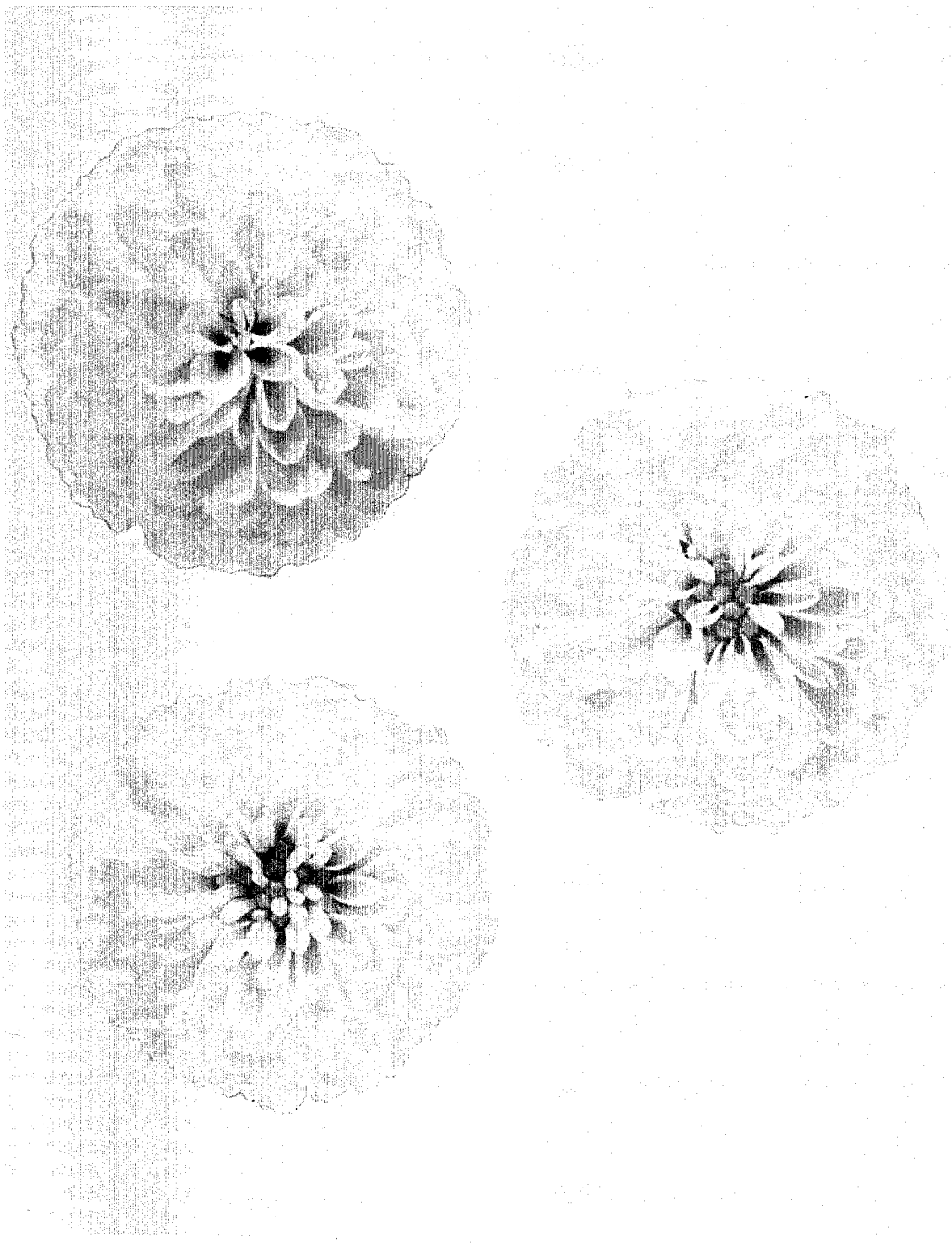

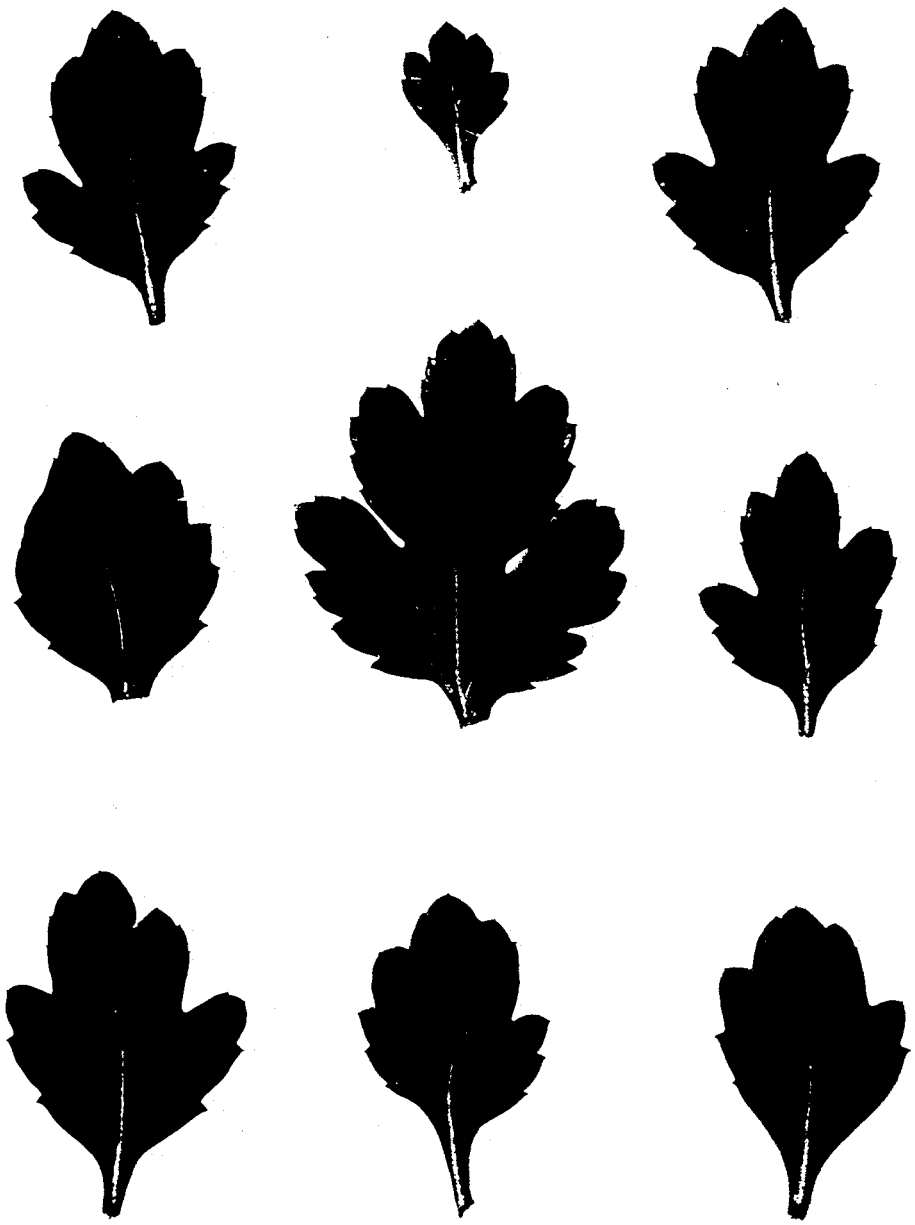

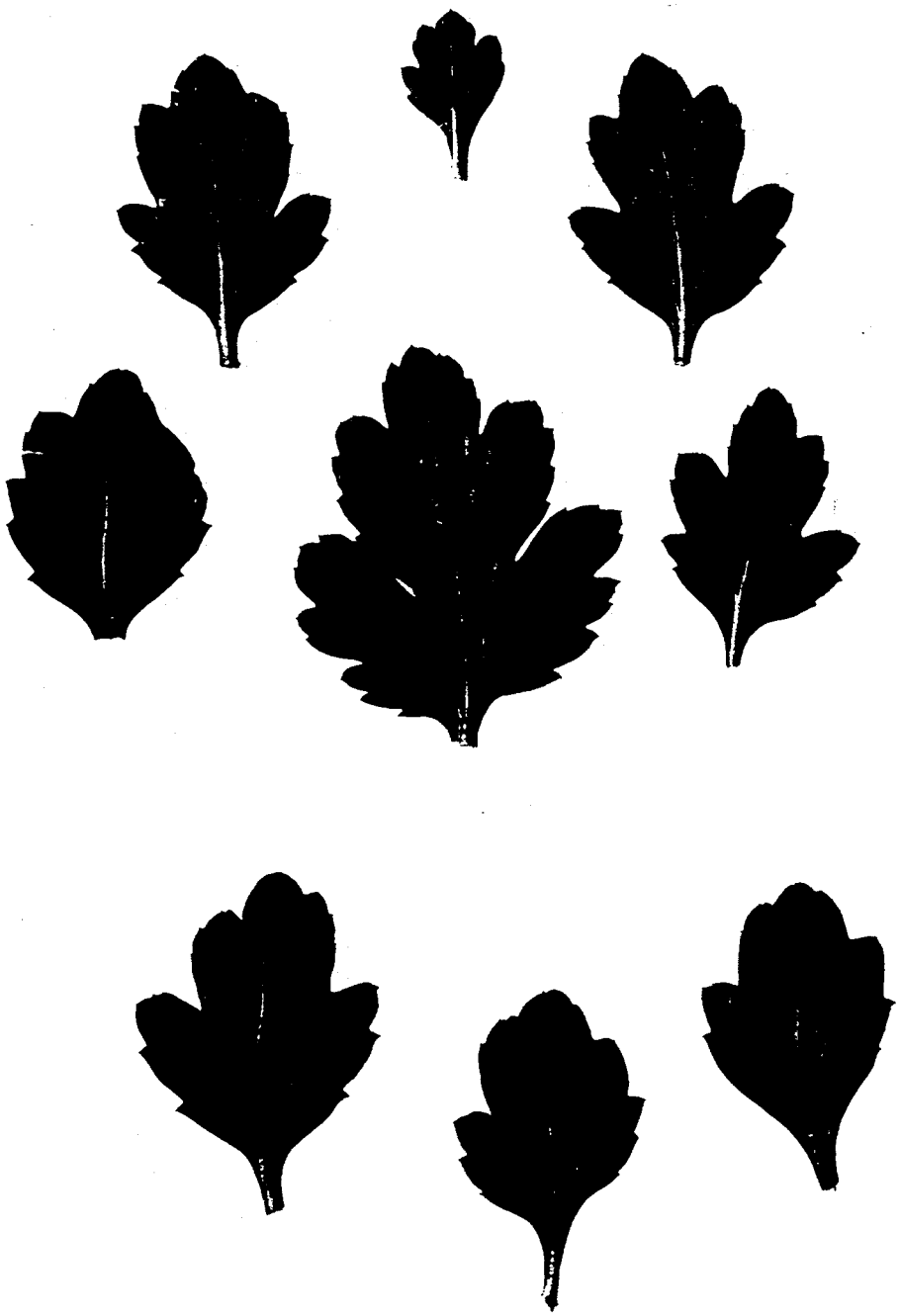

* * * * *